United States Patent [19]

Miyasaka et al.

[11] Patent Number: 5,318,972

[45] Date of Patent: * Jun. 7, 1994

[54] PYRIMIDINE NUCLEOSIDE DERIVATIVE AND ANTIVIRAL AGENT CONTAINING THE DERIVATIVE AS ACTIVE INGREDIENT

[75] Inventors: Tadashi Miyasaka; Hiromichi Tanaka, both of Yokohama, Japan; Erik D. A. De Clercq, Louvain, Belgium; Masanori Baba, Fukushima, Japan; Richard T. Walker, Birmingham, United Kingdom; Masaru Ubasawa, Yokohama, Japan

[73] Assignee: Mitsubishi Kasei Corporation, Tokyo, Japan

[ * ] Notice: The portion of the term of this patent subsequent to May 12, 2009 has been disclaimed.

[21] Appl. No.: 676,912

[22] Filed: Mar. 28, 1991

[30] Foreign Application Priority Data

Mar. 29, 1990 [JP] Japan .................. 2-81843
Jul. 27, 1990 [JP] Japan .................. 2-200896
Jul. 27, 1990 [JP] Japan .................. 2-200897

[51] Int. Cl.$^5$ .................. A61K 31/505; C07D 239/10
[52] U.S. Cl. .................. 514/269; 514/274; 544/302; 544/314
[58] Field of Search .................. 544/302, 314; 514/269, 514/274

[56] References Cited

U.S. PATENT DOCUMENTS

| 4,613,604 | 9/1986 | Chu et al. | 544/314 |
| 4,868,187 | 9/1989 | Ogilvie | 544/314 |

FOREIGN PATENT DOCUMENTS

| 0348170 | 12/1989 | European Pat. Off. . |  |
| 0371139 | 6/1990 | European Pat. Off. . |  |
| 0375329 | 6/1990 | European Pat. Off. . |  |
| 232492 | 1/1986 | German Democratic Rep. . |  |
| 0039672 | 3/1983 | Japan | 544/314 |
| 8909213 | 5/1989 | PCT Int'l Appl. . |  |

OTHER PUBLICATIONS

Chu et al, J. Hetero cyclic chemistry 23, 289–319, 1986.
Drabikowaka et al, Chemical Abstract, 107, 1987 #129717w.

Primary Examiner—Mukund J. Shah
Assistant Examiner—Y. N. Gupta
Attorney, Agent, or Firm—David G. Conlin

[57] ABSTRACT

A pyrimidine nucleoside derivative and pharmaceutically acceptable salt thereof specified by the presence of ethyl group or isopropyl group at 5-position of the pyrimidine ring and the presence of a (substituted) phenylthio or a (substituted) benzyl group at 6-position of the pyrimidine ring is provided. The pyrimidine nucleoside derivative and pharmaceutically acceptable salt thereof show a markedly higher anti-retroviral activity than conventional analogous compounds and have a relatively low toxicity against the host cells, and therefore, are useful as an active ingredient of antiviral agent.

8 Claims, No Drawings

PYRIMIDINE NUCLEOSIDE DERIVATIVE AND ANTIVIRAL AGENT CONTAINING THE DERIVATIVE AS ACTIVE INGREDIENT

BACKGROUND OF THE INVENTION

The present invention relates to a novel pyrimidine nucleoside derivative and an antiviral agent containing the derivative as active ingredient.

Infectious diseases caused by human acquired immunodeficiency virus (HIV), which is a type of retrovirus, have recently become a serious social problem. A compound of 3'-deoxy-3'-azidothymidine is known as a nucleoside compound used in the clinical treatment for diseases caused by HIV-infection. However, this compound has side-effects since it also exhibits considerable strong toxicity in the host cells.

Although some 2',3'-dideoxyribonucleosides are known as nucleoside compounds exhibiting an antiretroviral activity, it is still necessary to develop a substance possessing a higher activity and lower toxicity to the host cell (Hiroaki Mitsuya, Bodily Defence, Vol. 4, pp. 213-223 (1987)).

On the other hand, various acyclonucleoside compounds have been synthesized since Acyclovir (acycloguanosine) was developed as an antiviral substance effective against herpes virus (C. K. Chu and S. J. Culter, J. Heterocyclic Chem., 23, p. 289 (1986)). However, no compound having a sufficient activity especially against retroviruses has yet been discovered.

Consequently, with the aim of providing an antiviral agent, especially an agent which has an effective antiviral activity against retroviruses, the present inventors have synthesized a wide variety of novel 6-substituted acyclopyrimidine nucleoside compounds and their antiretroviral activities have been investigated. As the results, the present inventors have found that such an object can be attained by a specific 6-substituted acyclopyrimidine nucleoside derivative (WO 89/09213).

As 6-substituted acyclopyrimidine nucleosides, 6-fluorine substituted derivatives and 6-alkylamino substituted derivatives (DD-A-232492) and 6-methyl substituted derivatives (C.A. 107, 129717w (1987)) are known, however, the antiviral activity of these compounds has not been described.

The present inventors have conducted intensive studies on the screening of compounds having antiviral activities, especially a compound having an anti-retroviral activity, and found that among the 6-substituted acyclopyrimidine nucleoside derivatives generically disclosed but not specifically disclosed in WO 89/09213, those pyrimidine nucleoside derivatives having ethyl group or isopropyl group at the 5-position of the pyrimidine ring and having (substituted) phenylthio group or (substituted) benzyl group showed markedly excellent anti-retroviral activities. The present invention has been accomplished based on this finding.

SUMMARY OF THE INVENTION

The present invention intends to provide a pyrimidine nucleoside derivative represented by the following formula (I):

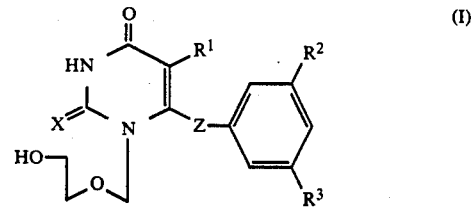

wherein $R^1$ represents ethyl group or isopropyl group; $R^2$ and $R^3$ independently represent hydrogen atom, an $C_1$-$C_3$ alkyl group or chlorine atom; X represents oxygen atom or sulfur atom; and Z represents sulfur atom or methylene group; with the proviso that $R^2$ and $R^3$ do not simultaneously represent hydrogen atoms when X represents oxygen atom and Z represents sulfur atom.

The present invention intends to further provide an antiviral agent containing the pyrimidine nucleoside derivative as active ingredient.

DETAILED DESCRIPTION OF THE INVENTION

The pyrimidine nucleoside derivative of the present invention is represented by the formula (I) shown above. In the formula (I), $C_1$-$C_3$ alkyl groups as the substitutents $R^2$ and $R^3$ may include methyl group, ethyl group, n-propyl group and isopropyl group.

The following Table 1 shows some illustrative examples of the derivative of the present invention.

TABLE 1

| Compound No. | $R^1$ | $R^2$ | $R^3$ | X | Z |
|---|---|---|---|---|---|
| 1 | —$C_2H_5$ | —H | —H | S | S |
| 2 | —$C_2H_5$ | —$CH_3$ | —$CH_3$ | O | S |
| 3 | —$C_2H_5$ | —$CH_3$ | —$CH_3$ | S | S |
| 4 | —$C_2H_5$ | —$CH_3$ | —H | O | S |
| 5 | —$C_2H_5$ | —$CH_3$ | —H | S | S |
| 6 | —$C_2H_5$ | —Cl | —Cl | O | S |
| 7 | —$C_2H_5$ | —Cl | —Cl | S | S |
| 8 | —$C_2H_5$ | —Cl | —H | O | S |
| 9 | —$C_2H_5$ | —Cl | —H | S | S |
| 10 | —$C_2H_5$ | —H | —H | O | $CH_2$ |
| 11 | —$C_2H_5$ | —H | —H | S | $CH_2$ |
| 12 | —$C_2H_5$ | —$CH_3$ | —$CH_3$ | O | $CH_2$ |
| 13 | —$C_2H_5$ | —$CH_3$ | —$CH_3$ | S | $CH_2$ |
| 14 | —$C_2H_5$ | —$CH_3$ | —H | O | $CH_2$ |
| 15 | —$C_2H_5$ | —$CH_3$ | —H | S | $CH_2$ |
| 16 | —$C_2H_5$ | —Cl | —Cl | O | $CH_2$ |
| 17 | —$C_2H_5$ | —Cl | —Cl | S | $CH_2$ |
| 18 | —$C_2H_5$ | —Cl | —H | O | $CH_2$ |
| 19 | —$C_2H_5$ | —Cl | —H | S | $CH_2$ |
| 20 | —CH(CH$_3$)$_2$ | —H | —H | S | S |
| 21 | —CH(CH$_3$)$_2$ | —$CH_3$ | —$CH_3$ | O | S |
| 22 | —CH(CH$_3$)$_2$ | —$CH_3$ | —$CH_3$ | S | S |

TABLE 1-continued

| Compound No. | R$^1$ | R$^2$ | R$^3$ | X | Z |
|---|---|---|---|---|---|
| 23 | -CH(CH$_3$)$_2$ | -CH$_3$ | -H | O | S |
| 24 | -CH(CH$_3$)$_2$ | -CH$_3$ | -H | S | S |
| 25 | -CH(CH$_3$)$_2$ | -Cl | -Cl | O | S |
| 26 | -CH(CH$_3$)$_2$ | -Cl | -Cl | S | S |
| 27 | -CH(CH$_3$)$_2$ | -Cl | -H | O | S |
| 28 | -CH(CH$_3$)$_2$ | -Cl | -H | S | S |
| 29 | -CH(CH$_3$)$_2$ | -H | -H | O | CH$_2$ |
| 30 | -CH(CH$_3$)$_2$ | -H | -H | S | CH$_2$ |
| 31 | -CH(CH$_3$)$_2$ | -CH$_3$ | -CH$_3$ | O | CH$_2$ |
| 32 | -CH(CH$_3$)$_2$ | -CH$_3$ | -CH$_3$ | S | CH$_2$ |
| 33 | -CH(CH$_3$)$_2$ | -CH$_3$ | -H | O | CH$_2$ |
| 34 | -CH(CH$_3$)$_2$ | -CH$_3$ | -H | S | CH$_2$ |
| 35 | -CH(CH$_3$)$_2$ | -Cl | -Cl | O | CH$_2$ |
| 36 | -CH(CH$_3$)$_2$ | -Cl | -Cl | S | CH$_2$ |
| 37 | -CH(CH$_3$)$_2$ | -Cl | -H | O | CH$_2$ |
| 38 | -CH(CH$_3$)$_2$ | -Cl | -H | S | CH$_2$ |

The pyrimidine nucleoside derivative of the present invention can be synthesized for instance in accordance with the following reaction scheme (1), (2) or (3).

(1) When Z in the formula (I) is sulfur atom.

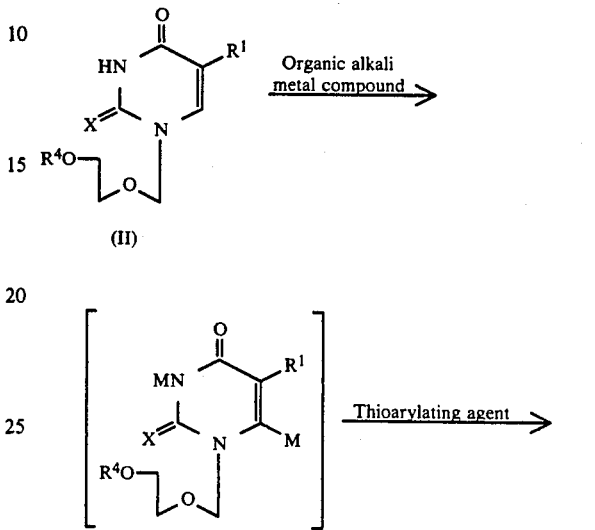

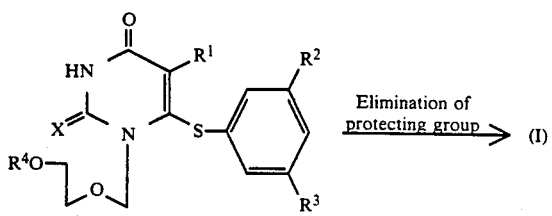

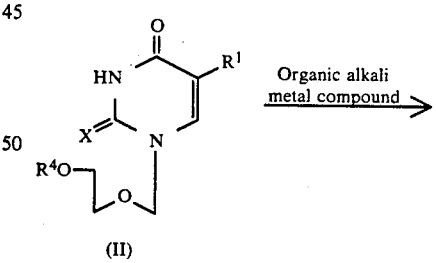

(2) When Z in the formula (I) is a methylene group.

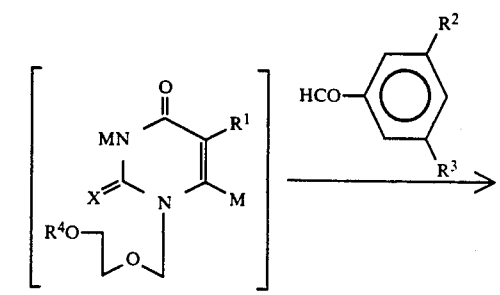

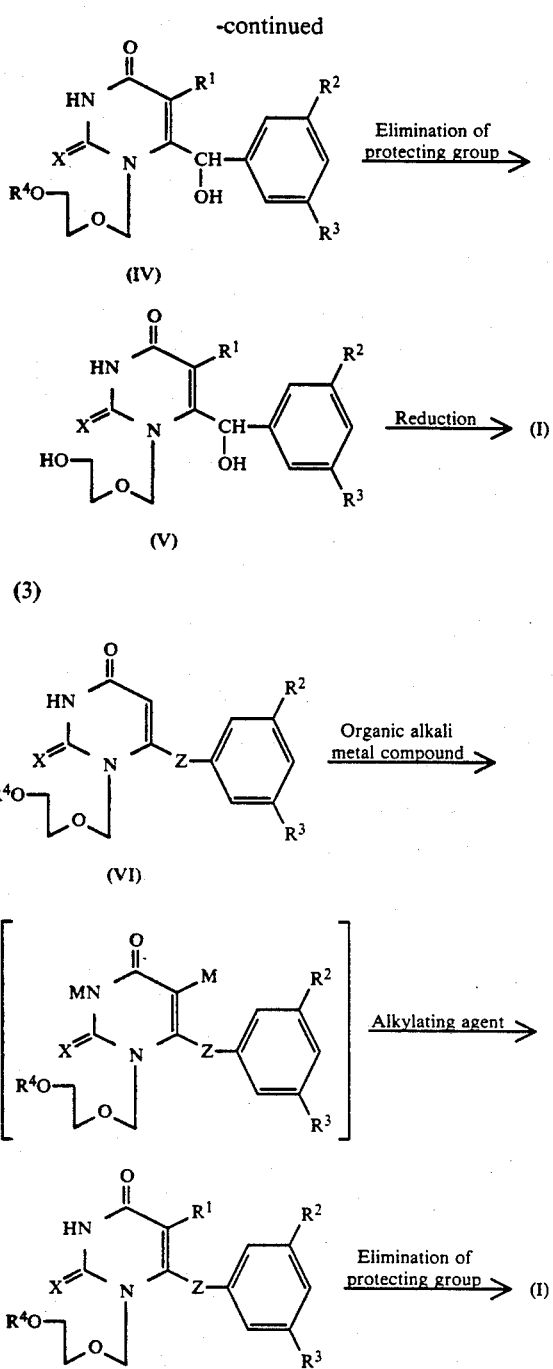

In the above reaction schemes, $R^1$, $R^2$, $R^3$ and X represent the same as defined in the formula (I), $R^4$ represents a protection group for a hydroxyl group and M represents an alkali metal.

The protecting group expressed by $R^4$ in the above reaction schemes may be selected from protecting groups usually used for protecting alcohol, provided that they do not undergo elimination under alkaline conditions.

Illustrative examples of such protecting groups may include aralkyl groups such as benzyl, trityl, monomethoxytrityl, dimethoxytrityl, trimethoxytrityl and the like; silyl groups such as trimethylsilyl, triethylsilyl, t-butyldimethylsilyl, t-butyldiphenylsilyl, dimethylphenylsilyl and the like; tetrahydropyranyl; and substituted alkyl groups such as methoxymethyl and the like. Of these, silyl groups may be most preferable.

As the first step of the synthesis of the pyrimidine nucleoside derivative of the present invention, a compound represented by the above general formula (II) or (VI) is allowed to react with an organic alkali metal compound at a temperature of from −80° C. to −10° C. for 0.2 to 10 hours in a solvent, for example, an ether solvent such as diethyl ether, tetrahydrofuran and the like. The organic alkali metal compound may include potassium bistrimethylsilylamide, sodium bistrimethylsilylamide and lithium alkylamides. Of these, lithium diisopropyl amide (LDA) and lithium 2,2,6,6-tetramethylpiperidide (LTMP) may be most preferable. A lithium alkylamide may preferably be prepared just before its use in the reaction system. For example, a preferable lithium alkylamide may be prepared by allowing a secondary amine such as diisopropylamine to react with an alkyl lithium for instance n-butyl lithium, at a temperature of from −80° C. to −10° C. for 0.2 to 5 hours with stirring in a solvent such as diethyl ether, dioxane, tetrahydrofuran, dimethoxyethane or the like under an atmosphere of inert gas such as argon gas.

The organic alkali metal compound may generally be used in an amount of from 2 to 5 moles per one mole of a compound represented by the general formula (II) or (VI).

Next, about 1 to 5 moles of a thioarylating agent, (substituted) benzaldehyde or an alkylating agent is added to one mole of a compound represented by the general formula (II) or (VI), and these compounds are allowed to react each other under similar conditions to the reaction of the organic alkali metal compound. The thioarylating agent may include diphenyl disulfide, a benzenesulfenyl halide and the like, each of which may have at least one substituent of $R^2$ and $R^3$.

Illustrative examples of the alkylating agent may include alkyl halides such as ethyl chloride, isopropyl chloride, ethyl bromide, isopropyl bromide, ethyl iodide, isopropyl iodide and the like; and alkyl sulfonates such as ethyl mesylate, isopropyl mesylate, ethyl tosylate, isopropyl tosylate and the like.

The compound represented by the general formula (II) as a starting material may be prepared by known methods. For example, such a starting compound of the formula (II) can be obtained by carrying out condensation reaction of a trimethylsilylated uracil derivative with (2-acetoxyethoxy)methylbromide, hydrolyzing the condensed product and then introducing the aforementioned protecting group. Such preparation processes have been disclosed in detail for instance in Can. J. Chem., vol. 60, 547 (1982).

Introduction of a protecting group can be carried out in the usual way. For example, a silyl protecting group can be introduced by allowing a compound to react with 1 to 10 times by mole of a silylating agent such as trimethylsilyl chloride, t-butyldimethylsilyl chloride or the like in a solvent such as dimethylformamide, acetonitrile, tetrahydrofuran or the like or in a mixture thereof, at a reaction temperature of from 0° to 50° C. in the presence of a base such as pyridine, picoline, diethylaniline, dimethylaniline, triethylamine, imidazole or the like. The compound represented by the general formula(VI) can be synthesized in similar manner to the process of the reaction scheme (1).

Prior to the elimination of a protecting group, the thus prepared compounds represented by the general formulae (III), (IV) and (VII) are subjected, if necessary, to separation and purification steps usually used for the separation and purification of nucleosides, such as recrystallization, adsorption chromatography, ion exchange chromatography and the like.

Elimination of the protecting group may be carried out by selecting a suitable method from usually used methods such as acid hydrolysis, ammonium fluoride treatment, catalytic reduction and the like, depending on the protecting group to be removed.

The compound represented by the general formula (V) which has been derived from the compound (IV) according to the reaction scheme (2) is further subjected to a reduction step to obtain the pyrimidine nucleoside derivative of the present invention represented by the general formula (I). Reduction of the compound (V) may be effected for instance by using hydrogen in the presence of palladium carbon, palladium hydroxide or the like.

The thus prepared pyrimidine nucleoside derivative of the present invention represented by the general formula (I) can be separated and purified by a method usually used for the separation and purification of nucleosides, such as recrystallization and adsorption or ion exchange chromatography.

The pyrimidine nucleoside derivative of the present invention may be made into a pharmaceutically acceptable salt by conventional methods. Examples of such salts may include alkali metal salts such as sodium salt, potassium salt and the like; alkaline earth metal salts such as magnesium salt and the like; and ammonium salts such as ammonium salt, methylammonium salt, dimethylammonium salt, trimethylammonium salt, tetramethylammonium salt and the like.

The pyrimidine nucleoside derivative of the present invention can be administered to a patient through any of the usual routes such as oral, rectal, parenteral and local administrations for the purpose of preventing infection of retroviruses and the like or treating infectious diseases caused by these viruses. Though it must be decided depending on the age, physical condition, body weight and the like of each patient, appropriate administration dose of the derivative of the present invention may be generally in the range of from 1 to 100 mg/kg(body weight)/day, preferably from 5 to 50 mg/kg(body weight)/day. Administration of the derivative of the present invention may be made once a day or a few times a day within the above range of dose.

For the purpose of formulating pharmaceutical preparations, the derivative of the present invention may be made into a composition containing usually used carriers, excipients and other additive agents. The carriers may be in either a solid or a liquid form. Illustrative examples of solid carriers may include lactose, china clay (kaolin), sucrose, crystalline cellulose, corn starch, talc, agar, pectin, stearic acid, magnesium stearate, lecithin, sodium chloride and the like. Illustrative examples of liquid carriers may include glycerin, peanut oil, polyvinyl pryrrolidone, olive oil, ethanol, benzyl alcohol, propylene glycol, water and the like.

The antiviral agent of the present invention can be made into various forms. When solid carriers are used, for example, the antiviral agent can be made into tablet, powder, granule, capsule, suppository, troche and the like. When liquid carriers are used, it can be made into syrup, emulsion, soft gelatin capsule, cream, gel, paste, spray and the like, as well as injection solution.

The present invention will be further illustrated hereinafter referring to the following non-limitative Examples.

EXAMPLE 1

Preparation of 5-ethyl-1-[(2-hydroxyethoxy)methyl]-6-phenylthio-2-thiouracil (compound No. 1 in Table 1)

To 6.2 g (40 mmol) of 5-ethyl-2-thiouracil suspended in 100 ml of dichloromethane was added 22 ml (88 mmol) of bis-(trimethylsilyl)-acetamide under a nitrogen atmosphere at room temperature, and the mixture was stirred for 3 hours. To this was further added gently 3.4 ml (48 mmol) of 1,3-dioxolan and 5.6 ml (48 mmol) of tin tetrachloride. The resulting mixture was then subjected to reflux for 17 hours. The reaction mixture thus obtained was poured into 100 ml of a mixture of methanol and water (1:1) containing 22 g of sodium bicarbonate. After stirring for 2 hours, the resulting mixture was filtered through sellaite and the filtrate was evaporated to dryness. To the residue was added 120 ml of acetonitrile, 12 g (80 mmol) of t-butyldimethylsilyl chloride and 5.4 g (80 mmol) of imidazole under a nitrogen atmosphere at room temperature. After 14 hours of stirring, the resulting reaction mixture was concentrated and subjected to partition using an ethyl acetate-water system, and then the organic layer was evaporated to dryness. The residue was adsorbed on a silica gel column and eluted with chloroform. Thereafter, the eluent was subjected to crystallization from a chloroform-hexane solvent to obtain 7.2 g (52%) of 1-[(2-t-butyldimethylsilyloxyethoxy)methyl]-5-ethyl-2-thiouracil.

Next, 11 ml (22 mmol) of 2.0M solution of lithium diisopropylamide in tetrahydrofuran was added under a nitrogen atmosphere to 30 ml of tetrahydrofuran which has been cooled down to −70° C. in advance. To this was added dropwise 14 ml of tetrahydrofuran solution containing 3.4 g (10 mmol) of the thus obtained 1-[(2-t-butyldimethylsilyloxyethoxy)methyl]-5-ethyl-2-thiouracil by keeping the reaction solution at a temperature of −70° C. or lower. The resulting mixture was stirred for 1 hour at −70° C. To this was added dropwise 10 ml of tetrahydrofuran solution containing 2.8 g (13 mmol) of diphenyl disulfide. After 1 hour, the resulting reaction mixture was further mixed with 1.3 ml of acetic acid, adjusted to room temperature and subjected to partition using an ethyl acetate-water system, and then the organic layer was evaporated to dryness. Thereafter, the residue was adsorbed on a silica gel column and eluted with chloroform to obtain 3.4 g (76%) of 1-[(2-t-butyldimethylsilyloxyethoxy)methyl]-5-ethyl-6-phenylthio-2-thiouracil.

A 0.42 g (0.94 mmol) portion of the thus obtained compound was dissolved in 5 ml of methanol, and the solution was adjusted to pH 1 with 1N HCl. Thereafter, the solution was evaporated to dryness and then subjected to crystallization from an ethyl acetate-hexane solvent to obtain 0.19 g (60%) of the titled compound. The melting point of the obtained compound was determined to be 71° to 75° C.

EXAMPLE 2

Preparation of
6-(3,5-dimethylphenylthio)-5-ethyl-1-[(2-hydroxyethoxy)methyl]uracil (compound No. 2 in Table 1)

The titled compound, having the melting point of 121° to 125° C., was obtained by repeating the process of Example 1 except that 5-ethyluracil was used instead of 5-ethyl-2-thiouracil and that 3,3',5,5'-tetramethyldiphenyl disulfide was used instead of diphenyl disulfide.

EXAMPLE 3

Preparation of
6-(3,5-dimethylphenylthio)-5-ethyl-1-[(2-hydroxyethoxy)methyl]-2-thiouracil (compound No. 3 in Table 1)

The titled compound, having the melting point of 121° to 123° C., was obtained by repeating the process of Example 1 except that diphenyl disulfide was replaced by 3,3',5,5'-tetramethyldiphenyl disulfide.

EXAMPLE 4

Preparation of
6-(3,5-dichlorophenylthio)-5-ethyl-1-[(2-hydroxyethoxy)methyl]uracil (compound No. 6 in Table 1)

The titled compound, having the melting point of 93° to 95° C., was obtained by repeating the process of Example 1 except that 5-ethyluracil was used instead of 5-ethyl-2-thiouracil and that 3,3',5,5'-tetrachlorodiphenyl disulfide was used instead of diphenyl disulfide.

EXAMPLE 5

Preparation of
6-(3,5-dichlorophenylthio)-5-ethyl-1-[(2-hydroxyethoxy)methyl]-2-thiouracil (compound No. 7 in Table 1)

The titled compound, having the melting point of 91° to 93° C., was obtained by repeating the process of Example 1 except that diphenyl disulfide was replaced by 3,3',5,5'-tetrachlorodiphenyl disulfide.

EXAMPLE 6

Preparation of
6-benzyl-5-ethyl-1-[(2-hydroxyethoxy)methyl]uracil (compound No. 10 in Table 1)

To 5.6 g (40 mmol) of 5-ethyluracil suspended in 100 ml of dichloromethane was added 22 ml (88 mmol) of bis-(trimethylsilyl)-acetamide under a nitrogen atmosphere at room temperature, and the mixture was stirred for 3 hours. To this was further added gently 3.4 ml (48 mmol) of 1,3-dioxolan and 5.6 ml (48 mmol) of tin tetrachloride. The resulting mixture was then subjected to reflux for 17 hours. The reaction mixture thus obtained was poured into 100 ml of a mixture of methanol and water (1:1) containing 22 g of sodium bicarbonate. After stirring for 2 hours, the resulting mixture was filtered through sellaite and the filtrate was evaporated to dryness. To the residue was added 120 ml of acetonitrile, 12 g (80 mmol) of t-butyldimethylsilylchloride and 5.4 g (80 mmol) of imidazole under a nitrogen atmosphere at room temperature. After 14 hours of stirring, the resulting reaction mixture was concentrated and subjected to partition using an ethyl acetate-water system, and then the organic layer was evaporated to dryness. The residue was adsorbed on a silica gel column and eluted with chloroform. Thereafter, the eluent was subjected to crystallization from a chloroform-hexane solvent to obtain 6.9 g (52%) of 1-[(2-t-butyldimethylsilyloxyethoxy)methyl]-5-ethyluracil.

Next, 11 ml (22 mmol) of 2.0M solution of lithium diisopropylamide in tetrahydrofuran was added under a nitrogen atmosphere to 30 ml of tetrahydrofuran which has been cooled down to −70° C. in advance. To this was added dropwise 14 ml of tetrahydrofuran solution containing 3.3 g (10 mmol) of the thus obtained 1-[(2-t-butyldimethylsilyloxyethoxy)methyl]-5-ethyluracil by keeping the reaction solution at a temperature of −70° C. or lower. The resulting mixture was stirred for 1 hour at −70° C. To this was dropwisely added 10 ml of tetrahydrofuran solution containing 1.3 ml (13 mmol) of benzaldehyde. After 1 hour, the resulting reaction mixture was further mixed with 1.3 ml of acetic acid, adjusted to room temperature and subjected to partition using an ethyl acetate-water system, and then the organic layer was evaporated to dryness. Thereafter, the residue was adsorbed on a silica gel column and eluted with chloroform to obtain 2.7 g (61%) of 1-[(2-t-butyldimethylsilyloxyethoxy)methyl]-5-ethyl-6-[(1-hydroxy-1-phenyl)-methyl]uracil.

A 2.7 g (6.1 mmol) portion of the thus obtained compound was dissolved in 15 ml of methanol. The resulting solution was adjusted to pH 1 with 1N HCl, allowed to stand for 1 hour at room temperature and then neutralized with a sodium hydroxide solution. Thereafter, the thus neutralized solution was evaporated to dryness and then subjected to crystallization from an ethyl acetatehexane solvent to obtain 1.8 g (90%) of 5-ethyl-1-[(hydroxyethoxy)methyl]-6-[(1-hydroxy-1-phenyl)-methyl]uracil.

A 1.8 g (5.5 mmol) portion of the thus obtained compound was dissolved in 75 ml of ethanol. The resulting solution was added with 0.2 g of a 20% palladium hydroxide-carbon catalyst and the mixture was stirred at 60° C. for 14 hours under a hydrogen atmosphere. The catalyst in the reaction mixture was removed by filtration. Thereafter, the filtrate was evaporated to dryness and then subjected to crystallization from an ethyl acetate-hexane solvent to obtain 1.6 g (93%) of the titled compound. The melting point of the obtained compound was determined to be 121° to 121.5° C.

EXAMPLE 7

Preparation of
6-(3,5-dimethylbenzyl)-5-ethyl-1-[(2-hydroxyethoxy)methyl]uracil (Compound No. 12 in Table 1)

The titled compound, having the melting point of 175° to 177° C., was obtained by repeating the process of Example 6 except that 3,5-dimethylbenzaldehyde was used instead of benzaldehyde.

EXAMPLE 8

Preparation of
1-[(2-hydroxyethoxy)methyl]-6-phenylthio-5-isopropyl-2-thiouracil (Compound No. 20 in Table 1)

The titled compound, having the melting point of 145° to 147° C., was obtained by repeating the process of Example 1 except that 5-isopropyl-2-thiouracil was used instead of 5-ethyl-2-thiouracil.

EXAMPLE 9

Preparation of 6-(3,5-dimethylphenylthio)-1-[(2-hydroxyethoxy)methyl]-5-isopropyluracil (Compound No. 21 in Table 1)

The titled compound, having the melting point of 138° to 139° C., was obtained by repeating the process of Example 1 except that 5-isopropyluracil was used instead of 5-ethyl-2-thiouracil and that 3,3',5,5'-tetramethyldiphenyl disulfide was used instead of diphenyl disulfide.

EXAMPLE 10

Preparation of 6-(3,5-dimethylphenylthio)-1-[(2-hydroxyethoxy)methyl]-5-isopropyl-2-thiouracil (Compound No. 22 in Table 1)

The titled compound, having the melting point of 140° to 141° C., was obtained by repeating the process of Example 1 except that 5-isopropyl-2-thiouracil was used instead of 5-ethyl-2-thiouracil and that 3,3',5,5'-tetramethyldiphenyl disulfide was used instead of diphenyl disulfide.

EXAMPLE 11

Preparation of 6-(3,5-dimethylbenzyl)-1-[(2-hydroxyethoxy)methyl]-5-isopropyluracil (Compound No. 31 in Table 1)

The titled compound, having the melting point of 187.5° to 188.5° C., was obtained by repeating the process of Example 6 except that 5-isopropyluracil was used instead of 5-ethyluracil and that 3,3',5,5'-tetramethylbenzaldehyde was used instead of benzaldehyde.

SYNTHETIC EXAMPLE 1

Preparation of 5-ethyl-1-[(2-hydroxyethoxy)methyl]-6-(phenylthio)uracil (compound No. 39)

To 5.6 g (40 mmol) of 5-ethyluracil suspended in 100 ml of dichloromethane was added 22 ml (88 mmol) of bis-(trimethylsilyl)acetamide under a nitrogen atmosphere at room temperature, and the mixture was stirred for 3 hours. To this was further added gently 3.4 ml (48 mmol) of 1,3-dioxolan and 5.6 ml (48 mmol) of tin tetrachloride. The resulting mixture was then subjected to reflux for 17 hours. The reaction mixture thus obtained was poured into 100 ml of a mixture of methanol and water (1:1) containing 22 g of sodium bicarbonate. After stirring for 2 hours, the resulting mixture was filtered through sellaite and the filtrate was evaporated to dryness. To the residue was added 120 ml of acetonitrile, 12 g (80 mmol) of t-butyldimethylsilyl chloride and 5.4 g (80 mmol) of imidazole under a nitrogen atmosphere at room temperature. After 14 hours of stirring, the resulting reaction mixture was concentrated and subjected to partition using an ethyl acetate-water system, and then the organic layer was evaporated to dryness. The residue was adsorbed on a silica gel column and eluted with chloroform. Thereafter, the eluent was subjected to crystallization from a chloroform-hexane solvent to obtain 6.9 g (52%) of 1-[(2-t-butyldimethylsilyloxyethoxy)methyl]-5-ethyluracil.

Next, 11 ml (22 mmol) of 2.0M solution of lithium diisopropylamide in tetrahydrofuran was added under a nitrogen atmosphere to 30 ml of tetrahydrofuran which has been cooled down to −70° C. in advance. To this was added dropwise 14 ml of tetrahydrofuran solution containing 3.3 g (10 mmol) of the thus obtained 1-[(2-t-butyldimethylsilyloxyethoxy)methyl]-5-ethyluracil by keeping the reaction solution at a temperature of −70° C. or lower. The resulting mixture was stirred for 1 hour at −70° C. To this was dropwisely added 10 ml of tetrahydrofuran solution containing 2.8 g (13 mmol) of diphenyl disulfide. After 1 hour, the resulting reaction mixture was further mixed with 1.3 ml of acetic acid, adjusted to room temperature and subjected to partition using an ethyl acetate-water system, and then the organic layer was evaporated to dryness. Thereafter, the residue was adsorbed on a silica gel column and eluted with chloroform to obtain 3.4 g (76%) of 1-[(2-t-butyldimethylsilyloxyethoxy)methyl]-5-ethyl-6-(phenylthio)uracil.

A 0.41 g (0.94 mmol) portion of the thus obtained compound was dissolved in 5 ml of methanol, and the solution was adjusted to pH 1 with 1N HCl. Thereafter, the solution was evaporated to dryness and then subjected to crystallization from an ethyl acetate-hexane solvent to obtain 0.18 g (60%) of the titled compound. The melting point of the obtained compound was determined to be 117° to 120° C.

SYNTHETIC EXAMPLE 2

Preparation of 1-[(2-hydroxyethoxy)methyl]-6-phenylthio-5-isopropyluracil (compound No. 40)

The titled compound, having the melting point of 85° to 87° C., was obtained by repeating the process of Synthetic Example 1 except that 5-isopropyluracil was used in place of 5-ethyluracil.

EXAMPLE 12

Preparation of tablet

| | |
|---|---|
| 5-Ethyl-1-[(2-hydroxyethoxy)methyl]-6-phenylthio-2-thiouracil | 10 g |
| Corn starch | 65 g |
| Carboxycellulose | 20 g |
| Polyvinyl pyrrolidone | 3 g |
| Calcium stearate | 2 g |
| Total weight | 100 g |

The above components were well mixed and tablets were produced by a direct tableting method. Each tablet thus prepared had a weight of 100 mg and contained 1.0 mg of 5-ethyl-1-[(2-hydroxyethoxy)methyl]-6-phenylthio-2-thiouracil.

EXAMPLE 13

Preparation of powder and capsule

| | |
|---|---|
| 5-Ethyl-1-[(2-hydroxyethoxy)methyl]-6-phenylthio-2-thiouracil | 20 g |
| Crystalline cellulose | 80 g |
| Total weight | 100 g |

Both powder components were well mixed to obtain a powder formulation. Capsule was obtained by encapsulating 100 mg of the thus obtained powder into a hard capsule of No. 5.

EXAMPLE 14

Preparation of tablet

| | |
|---|---|
| 5-Ethyl-1-]-(2-hydroxyethoxy)methyl]-6 phenylthiouracil | 10 g |
| Corn starch | 65 g |
| Carboxycellulose | 20 g |
| Polyvinyl pyrrolidone | 3 g |
| Calcium stearate | 2 g |
| Total weight | 100 g |

The above components were well mixed and tablets were produced by a direct tableting method. Each tablet thus prepared had a weight of 100 mg and contained 1.0 mg of 5-ethyl-1-[(2-hydroxyethoxy)methyl]-6-(phenylthio)uracil.

EXAMPLE 15

Preparation of powder and capsule

| | |
|---|---|
| 5-Ethyl-1-[(2-hydroxyethoxy)methyl]-6-phenylthiouracil | 20 g |
| Crystalline cellulose | 80 g |
| Total weight | 100 g |

Both powder components were well mixed to obtain a powder formulation. Capsule was obtained by encapsulating 100 mg of the thus obtained powder into a hard capsule of No. 5.

EXAMPLE 16

Inhibitory activity for HIV infection

In RPMI 1640 DM culture medium containing 20 mM of Hepes buffer solution, 10% fetal bovine serum and 20 g/ml of gentamycin, $3 \times 10^4$ MT-4 cells (human T cell clone which is destroyed by the infection of HIV) were infected with HIV in an amount of 100 times as large as expected to cause 50% infection of the cells. Immediately thereafter, a predetermined amount of sample was added to the culture medium using 50 mg/ml sample solutions in dimethyl sulfoxide and the cells were cultured at 37° C.

After 5 days of incubation, the number of existing cells was counted to determine the concentration of the compound required for preventing the death of 50% of the MT-4 cells. Separately, MT-4 cells were cultured in the same way as above except that they were not infected with HIV to determine the concentration of the compound at which 50% of the MT-4 cells were destroyed.

The result are shown in Table 2 (compound numbers in Table 2 correspond to those in Table 1 and Examples).

TABLE 2

| Compound No. | 50% inhibitory concentration of HIV infection (μM) | 50% cytotoxic concentration to MT-4 cells (μM) |
|---|---|---|
| 1 | 0.11 | 148 |
| 2 | 0.013 | 149 |
| 3 | 0.0078 | 227 |
| 6 | 0.014 | 51 |
| 7 | 0.043 | 64 |
| 10 | 0.35 | 391 |
| 12 | 0.013 | 280 |
| 20 | 0.059 | 400 |
| 21 | 0.0027 | 128 |
| 22 | 0.0045 | 48 |
| 31 | 0.0066 | 318 |
| 39 | 0.077 | 221 |
| 40 | 0.063 | 231 |
| Reference compound 1* | 7.0 | >250 |
| Reference compound 2* | 0.98 | 125 |
| Reference compound 3* | 3.4 | 224 |
| Reference compound 4* | 13 | 282 |

Reference compound 1

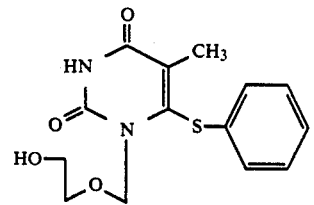

Reference compound 2

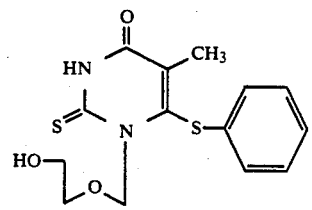

Reference compound 3

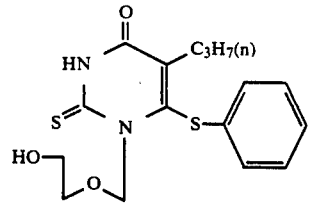

Reference compound 4

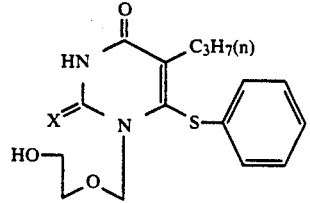

What is claimed is:

1. A pyrimidine nucleoside derivative represented by the following formula (I):

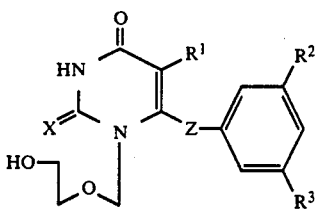
(I)

wherein R[1] represents ethyl group or isopropyl group; R[2] and R[3] independently represent hydrogen atom, an $C_1$–$C_3$ alkyl group or chlorine atom; X represents oxygen atom or sulfur atom; and Z represents sulfur atom or methylene group; with the proviso that R[2] and R[3] do not simultaneously represent hydrogen atoms when X represents oxygen atom and Z represents sulfur atom, or a pharmaceutically acceptable salt thereof.

2. 5-Ethyl-1-[(2-hydroxyethoxy)methyl]-6-phenylthio-2-thiouracil or a pharmaceutically acceptable salt thereof.

3. 1-[(2-Hydroxyethoxy)methyl]-6-phenylthio-5-isopropyl-2-thiouracil or a pharmaceutically acceptable salt thereof.

4. 6-(3,5-Dimethylphenylthio)-5-ethyl-1-[(2-hydroxyethoxy)methyl]uracil or a pharmaceutically acceptable salt thereof.

5. 6-(3,5-Dimethylphenylthio)-1-[(2-hydroxyethoxy)methyl]-5-isopropyluracil or a pharmaceutically acceptable salt thereof.

6. 6-Benzyl-5-ethyl-1-[(2-hydroxyethoxy)methyl]uracil or a pharmaceutically acceptable salt thereof.

7. An anti-retroviral agent comprising as an active ingredient an antivirally effective amount of the pyrimidine nucleoside derivative or the pharmaceutically acceptable salt according to claim 1, and a pharmaceutically acceptable carrier or adjuvant.

8. An anti-retroviral agent comprising as an active ingredient an antivirally effective amount of a pyrimidine derivative selected from the group consisting of 5-ethyl-1-[(2-hydroxyethoxy)methyl]-6-(phenylthio)uracil, 1-[(2-hydroxyethoxy)methyl]-6-phenylthio-5-isopropyluracil and a pharmaceutically acceptable salts thereof, and a pharmaceutically acceptable carrier or adjuvant.

* * * * *